United States Patent [19]

Dempf et al.

[11] 4,409,396

[45] Oct. 11, 1983

[54] PROCESS FOR THE MANUFACTURE OF UNSATURATED CARBOXYLIC ACID ESTERS

[75] Inventors: Dominik Dempf, Mehring; Ludwig Schmidhammer, Haiming; Gerhard Dummer, Burgkirchen; Günter Roscher, Kelkheim; Karl-Heinz Schmidt, Idstein; Ernst Selbertinger, Marktl; Rudolf Strasser, Burghausen, all of Fed. Rep. of Germany

[73] Assignees: Wacker-Chemie GmbH, Munich; Hoechst Aktiengesellschaft, Frankfurt, both of Fed. Rep. of Germany; a part interest

[21] Appl. No.: 299,019

[22] Filed: Sep. 3, 1981

[30] Foreign Application Priority Data

Sep. 26, 1980 [DE] Fed. Rep. of Germany ....... 3036421

[51] Int. Cl.$^3$ .......................................... C07C 67/055
[52] U.S. Cl. ............................ 560/245; 260/410.9 N; 560/241
[58] Field of Search .............................. 560/245, 241; 260/410.9 N

[56] References Cited

U.S. PATENT DOCUMENTS 3,642,878  2/1972  Mottern ............................... 560/245

FOREIGN PATENT DOCUMENTS 1793365  7/1973  Fed. Rep. of Germany ...... 560/245
1003347  9/1965  United Kingdom ................ 560/245
1110663  4/1968  United Kingdom ................ 560/245
1222984  2/1971  United Kingdom ................ 560/245

Primary Examiner—Michael L. Shippen
Attorney, Agent, or Firm—Allison C. Collard; Thomas M. Galgano

[57] ABSTRACT

The invention relates to a process for the manufacture of unsaturated carboxylic acid esters by the reaction of olefins or cyclo-olefins with oxygen and carboxylic acids in the gaseous phase, in the presence of a catalyst which contains elements of the subsidiary group VIII of the periodic system and/or compounds thereof, and an alkali metal acetate, at temperatures of from 100° to 250° C. and pressures of from 0.5 to 21 bar absolute, wherein from 1 to 8000 parts per million (by weight), calculated on the carboxylic acid used, of organic chlorine compounds are added to the reaction mixture.

5 Claims, No Drawings

PROCESS FOR THE MANUFACTURE OF UNSATURATED CARBOXYLIC ACID ESTERS

The invention relates to a process for the manufacture of unsaturated carboxylic acid esters by the reaction of olefins or cyclo-olefins with oxygen and carboxylic acids in the gaseous phase, in the presence of a catalyst which contains elements of subsidiary group VIII of the periodic system and/or compounds thereof, and an alkali metal acetate, at temperatures of from 100° to 250° C. and pressures of from 0.5 to 21 bar absolute.

The manufacture of unsaturated carboxylic acid esters by the reaction of olefins and oxygen with carboxylic acids on noble-metal contacts is known per se (cf. in this connection German Patentschrift 14 43 882). A number of proposals for improvement have also already been published: thus, for example, measures for increasing the space/time yield of the ester in the process are described in German Auslegeschrift 12 44 760 and German Offenlegungsschrift 23 15 037.

In addition to catalyst efficiency, other factors determine the efficiency of the process, however, such as the service life of the noble-metal catalyst and the olefin yield of the process. Thus, for example, in the case of the manufacture of vinyl acetate according to German Auslegeschrift No. 12 77 249, the degree of combustion of ethylene to form $CO_2$, which is of no value, is from 7 to 13%, calculated on reacted ethylene.

The object of the invention therefore was to lower the degree of combustion of the olefin used and also to lengthen the service life of the catalyst.

Surprisingly, it has now been found that the addition of organic chlorine compounds to the reaction system solves this problem.

The invention provides a process for the manufacture of unsaturated carboxylic acid esters, which is characterized in that the reaction is carried out in the presence of from 1 to 8000 parts per million, by weight, calculated on the carboxylic acid used, of organic chlorine compounds, individually or in admixture, selected from the group consisting of:

(a) α-chlorocarboxylic acids having from 1 to 4 carbon atoms and esters thereof with alcohols having from 1 to 4 carbons atoms;

(b) α-chloroaldehydes having from 1 to 4 carbon atoms;

(c) chlorine derivatives of methane having from 1 to 4 chlorine atoms;

(d) chlorine derivatives of methane having from 1 to 3 chlorine atoms and at least one fluorine atom; and (e) chlorine derivatives of ethane and of propane each having at least 2 chlorine atoms.

The chlorine compounds to be used according to the invention are preferably used in quantities of from 10 to 100 parts per million, by weight, calculated on the quantity of carboxylic acid.

It is also preferred that the addition of the organic chlorine compounds according to the invention be effected continuously.

The reaction of the olefin or cyclo-olefin with the oxygen and the carboxylic acid is effected, according to the process of the invention, in a manner known per se, at temperatures of from 100° to 250° C. in the gaseous phase and pressures of from 0.5 to 21 bar absolute, in the presence of a catalyst which contains elements of subsidiary group VIII of the periodic system and/or compounds thereof, and an alkali metal acetate.

The mixture used for the reaction usually contains a multiple excess of olefin. For this reason alone, the conversion to the corresponding unsaturated carboxylic acid ester is not quantitative, calculated on the olefin used. Unreacted olefin is therefore re-circulated admixed with, inter alia, carbon dioxide, nitrogen, argon and residual oxygen. Olefin is introduced into the system upstream of the reactor, according to its consumption. The mixture subsequently flows through a carboxylic acid saturator, for example one constructed in the form of a column, with the desired quantity of carboxylic acid being set by an appropriate temperature control. From 1 to 8000 ppm of organic chlorine compounds according to the invention are added to the carboxylic acid. If desired, the metering-in of the organic chlorine compounds according to the invention can alternatively be carried out at a different place, but still upstream of the reactor. Consumed oxygen is replenished by means of a mixing nozzle, generally in quantities of up to 7% by volume, calculated on the whole mixture. The mixture to which is advantageously added an activator solution, finally passes into a reactor which is charged with a catalyst which contains elements of subsidiary group VIII of the periodic system and/or compounds thereof, and an alkali-metal acetate. The mixture that leaves the reactor contains, as fundamental constituents, unsaturated carboxylic acid ester, unreacted olefin, carboxylic acid, residual oxygen, carbon dioxide, water and inert substances. The separation of the mixture is effected, first, by a condensation step in which the carboxylic acid ester, the carboxylic acid and the water are separated off. The recycle gas that remains is additionally subjected to a potash wash in order to remove $CO_2$. In order to maintain stationary conditions, inert substances, such as nitrogen, argon and others, are discharged by means of a partial current. The recycle gas is finally recirculated.

The above description of the process was made solely as an example with reference to conditions as used for carrying out the process within the framework of industrial production.

The invention is based on the recognition that the reaction of olefins or cyclo-olefins with oxygen and carboxylic acid in the gaseous phase under the reaction conditions according to the inventive process lowers the degree of combustion of olefin and increases the service life of the catalyst which contains the elements of subsidiary group VIII of the periodic system and/or compounds thereof and an alkali metal acetate. Those advantages may likewise be achieved with modifications of the process that lie within this scope.

Examples of organic chlorine compounds to be used according to the invention are chloroacetic acid, cichloroacetic acid, trichloroacetic acid, α-chloropropionic acid, α-chlorobutyric acid, α-chloroisobutyric acid, chloroacetic acid methyl ester, chloroacetic acid ethyl ester, chloroacetic acid propyl ester, dichloroacetic acid ethyl ester, chloroacetic acid butyl ester, α-chloropropionic acid methyl ester, α-chloropropionic acid ethyl ester, chloroacetaldehyde, dichloroacetaldehyde, trichloroacetaldehyde, α-chloropropionaldehyde, α-chlorobutyraldehyde, α-chloroisobutyraldehyde, methyl chloride, methylene chloride, chloroform, carbon tetrachloride, dichlorodifluoromethane, trichlorofluoromethane, chlorotrifluoromethane, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,2-dichloropropane, 1,3-dichloropropane, 1,1,2-trichloroethane and others.

As olefins or cyclo-olefins, there may be used according to the invention those which are gaseous under the conditions of the process. Examples are ethylene, propylene, butylene, isobutylene, pentene, hexene, cyclopentene, cyclohexene and others, but especially ethylene.

Examples of carboxylic acids are acetic acid, propionic acid and others.

According to the invention, support catalysts are preferably used. The catalysts contain elements of subsidiary group VIII of the periodic system and/or compounds thereof. Examples are the elements palladium, platinum, gold and others, and carboxylic acid salts thereof, especially acetates thereof. The catalysts also contain alkali metal acetates. Examples are the acetates of lithium, sodium, potassium, rubidium and caesium. Furthermore, the catalysts may contain additives of divalent metals, such as manganese or cadmium.

Aqueous potassium acetate solutions have proved to be suitable as activator solutions, in particular.

Examples of unsaturated carboxylic acid esters to be manufactured according to the invention are vinyl acetate, allyl acetate, butenyl acetate, pentenyl acetate, hexenyl acetate, cyclopentenyl acetate, cyclohexenyl acetate, vinyl propionate, vinyl butyrate, vinyl isobutyrate, allyl propionate, allyl butyrate, and others, but especially vinyl acetate.

The measures to be taken in order to introduce, into the reaction system, the organic chlorine compounds that are to be reacted according to the invention are familiar to the person skilled in the art. Examples of such measures are introduction by means of nozzles, injection and the like. It is also possible to use extraction techniques.

It is also possible to introduce the chlorine compounds together with other reactants, for example, together with the carboxylic acid to be reacted or together with the activator solution.

The addition may be effected continuously or discontinuously.

In the case of continuous addition of the organic chlorine compounds to be used according to the invention, quantities lying in the lower region according to the inventive process, preferably from 10 to 100 ppm, calculated on the quantity of carboxylic acid used, are sufficient. Advantageously, the organic chlorine compound is added to the desired quantity of carboxylic acid.

In the case of discontinuous addition, the higher quantities according to the inventive process are mostly used. The necessity for subsequent charging is indicated, for example, by the increasing $CO_2$ content of the reaction products.

By means of the process according to the invention, it is possible to reduce the degree of combustion of olefin. Accordingly, the yield of both the olefin and the oxygen is increased. Furthermore, the service life of the catalyst is lengthened with increased catalyst efficiency.

The invention will now be described in more detail with reference to the following examples and comparison examples.

EXAMPLE 1

Manufacture of vinyl acetate

A support catalyst is used that is based on bentonite and has the following active constituents, each in acetate form: 2.2% by weight of palladium, 1.7 to 1.9% by weight of cadmium, 0.07% by weight of manganese, and 1.9% by weight of postassium, each calculated on the quantity of catalyst. 19 m³ of the contact described above are introduced into the reactor. In addition, upstream of the reactor, approximately 15 kg/h of a 2% by weight aqueous solution of potassium acetate are introduced continuously by means of a nozzle. The circulation gas that is passed over the contact has the following composition:

63% by volume of ethylene;
12% by volume of acetic acid + organic chlorine compounds according to the invention;
8% by volume of $CO_2$;
6% by volume of oxygen; and
11% by volume of inert substances (nitrogen, argon, ethane) and water.

The quantity of recycle gas is 56,000 m³/h (measured at standard temperature and pressure).

The acetic acid is introduced into the system by saturating the recycle gas at a temperature of 115° C.

30 parts per million by weight of monochloroacetic acid are added to the acetic acid following to the acetic acid saturator. The temperature in the catalyst bed is maintained at 165° C. by correspondingly adjusting the vapor pressure in the outer casing of the reactor. The pressure of the system is 8 bar and is maintained by the continuous addition of 2780 m³/h (measured at standard temperature and pressure) of ethylene and 1847 m³/h (measured at standard temperature and pressure) of oxygen to the recycle gas. After leaving the reactor, the mixture is subjected to a condensation step yielding 23.3 t/h of crude vinyl acetate having the following composition:

42.9% by weight of vinyl acetate;
47.2% by weight of acetic acid; and
9.9% by weight of water.

The following specific consumption values and yields are achieved:

ethylene: 350.3 kg/t of vinyl acetate, corresponding to 92.94% by weight yield
oxygen: 263.9 kg/t of vinyl acetate, corresponding to 70.5% by weight yield
$CO_2$ formed: 49.1 kg/t of vinyl acetate.

The ethylene conversion is 7.9% by weight, calculated on the ethylene used.

The proportion of the ethylene combusted is 0.36% by weight, calculated on the ethylene used, and 4.5% by weight, calculated on the ethylene reacted.

After an operating period of 17,000 hours there is still catalyst efficiency as may be seen from the specific combustion values and yields given above.

COMPARISON EXAMPLE 1

Vinyl acetate is produced under substantially the same temperature and pressure conditions and on the same contact as described in Example 1, but with the modification that the operation is carried out without monochloroacetic acid.

56,000 m³/h (measured at standard temperature and pressure) of a recycle gas of the following composition:

65% by volume of ethylene;
12% by volume of acetic acid;
10% by volume of $CO_2$;
6.5% by volume of oxygen; and
6.5% by volume of inert substances (nitrogen, argon, ethane) and water are passed over the contact. In order to maintain the pressure conditions, 2937 m³/h (measured at standard temperature and pressure) of ethylene and 2392 m³ (measured at standard temperature and pressure) of oxygen are supplied.

Downstream from the reactor, 23.5 t/h of crude vinyl acetate having the following composition are obtained by condensation:
42.6% by weight of vinyl acetate;
46.8% by weight of acetic acid; and
10.6% by weight of water.

The following specific consumption values and yields are produced from those values:
ehtylene: 370.0 kg/t of vinyl acetate, corresponding to 88.0% by weight yield
oxygen: 341.8 kg/t of vinyl acetate, corresponding to 54.4% by weight
$CO_2$ formed: 100.1 kg/t of vinyl acetate.

Accordingly, the proportion of ethylene combusted is 0.69% by weight, calculated on the ethylene used, and 8.6% by weight, calculated on the ethylene reacted.

The operating period of the contact was 10,000 hours; in order to maintain the necessary space/time yield, it was necessary to raise the temperature in the reactor from an initial 165° C. gradually to 200° C.

EXAMPLE 2

Vinyl acetate is manfactured on the catalyst described according to Example 1, the following test apparatus being used:

A vertically arranged refined steel tube having an internal width of 25 mm and a length of 2500 mm serves as the reactor, which is charged with 1000 cm³ of catalyst. An intensive cooler is connected to the outlet of the reactor in order to separate off the condensable reaction products. The condensate is tested by gas chromatography for vinyl acetate. A gas burette for the collection of samples of waste gases is attached at the outlet of the cooler in order to measure the $CO_2$ content of the waste gas by gas chromatography. 3 liters/h of oxygen, 35 liters/h of ethylene and 13 liters/h of nitrogen are introduced at the reactor inlet. The nitrogen and ehtylene current is passed via a fritted flask, which contains acetic acid and is tempered to 70° C., in order, according to partial pressure, to introduce acetic acid into the reaction system with the gas current. Organic chlorine compounds according to the invention are added to the acetic acid.

The temperature in the catalyst bed is a constant 170° C. and is controlled by heating the casing of the reaction tube. The reaction is carried out at ambient pressure.

Results:

TABLE 1

| addition to acetic acid | addition in ppm calculated on acetic acid | $CO_2$ concentration in the waste gas | concentration of vinyl acetate in the condensate |
|---|---|---|---|
| — | — | 4.5% by vol. | 1.5% by wt. |
| chloro-acetic acid | 1000 | 4.0% by vol. | 1.8% by wt. |
| chloro-acetaldehyde | 1000 | 4.0% by vol. | 1.8% by wt. |
| chloro-acetic acid | 5000 | 3.0% by vol. | 2.2% by wt. |
| chloro-acetaldehyde | 5000 | 3.0% by vol. | 2.2% by wt. |
| $CCl_4$ | 100 | 4.05% by vol. | 1.95% by wt. |

TABLE 1-continued

| addition to acetic acid | addition in ppm calculated on acetic acid | $CO_2$ concentration in the waste gas | concentration of vinyl acetate in the condensate |
|---|---|---|---|
| $CHCl_3$ | 200 | 3.8% by vol. | 2.1% by wt. |

EXAMPLE 3

In the apparatus described in Example 2, vinyl acetate is manufactured on 1000 cm³ of a support catalyst which is manufactured in the following manner (cf. in this connection German Auslegeschrift No. 12 77 249):

1000 cm³ of silica support material in spherical form (4 mm diameter) are impregnated with an aqueous solution that contains 4 g of palladium (in the form of $PdCl_2$) and 1.5 g of gold (in the form of $H(AuCl_4)$). The material is subsequently reduced with 5% strength hydrazine hydrate solution and then dried and washed with distilled water until free of hydrazine. The product is then treated with an 11% aqueous potassium sodium acetate solution (molar ratio of sodium to potassium = 1:1) and finally dried in vacuo at 60° C.

Results

TABLE 2

| addition to acetic acid | addition in ppm calculated on acetic acid | $CO_2$ concentration in the waste gas | concentration of vinyl acetate in the condensate |
|---|---|---|---|
| — | — | 4.2% by vol. | 1.6% by wt. |
| dichloro-acetic acid | 5000 | 3.4% by vol. | 2.2% by wt. |
| dichloro-acetaldehyde | 5000 | 3.4% by vol. | 2.2% by wt. |
| $CF_2Cl_2$ | 50 | 3.3% by vol. | 2.05% by wt. |
| $C_2H_4Cl_2(1,2)$ | 100 | 3.6% by vol. | 1.95% by wt. |

EXAMPLE 4

In the arrangement described in Example 2, vinyl acetate is manufactured on a support catalyst based on magnesium spinel having 2% by weight of palladium and 2% by weight of sodium acetate as active constituents (cf. in this connection German Auslegeschrift No. 12 49 255).

Results

TABLE 3

| addition to acetic acid | addition in ppm calculated on acetic acid | $CO_2$ concentration in the waste gas | concentration of vinyl acetate in the condensate |
|---|---|---|---|
| — | — | 4.4% by vol. | 1.55% by wt. |
| $C_2HCl_5$ | 8000 | 3.8% by vol. | 1.95% by wt. |
| 1,1,2-trichloropropane | 5000 | 3.6% by vol. | 2.2% by wt. |

By comparison with the blank tests given in the first row of each table, the results of Examples 2, 3 and 4 show that the addition of organic chlorine compounds according to the invention both increases the yield of vinyl acetate and lowers the degree of combustion of ethylene.

EXAMPLE 5

Allyl acetate is prepared in the experimental arangement described in Example 2, but propylene is used as the olefin, instead of ethylene. The catalysts described according to Examples 2, 3 and 4 are used.

Results

TABLE 4

| catalyst | addition to acetic acid | addition in ppm, calculated on acetic acid | $CO_2$ concentration in the waste gas | allyl acetate concentration in the condensate |
|---|---|---|---|---|
| according to Example 1 | — | — | 4.6% by vol. | 1.3% by wt. |
| according to Example 1 | chloroacetic acid | 5000 | 3.1% by vol. | 1.8% by wt. |
| according to Example 3 | chloroacetaldehyde | 5000 | 3.1% by vol. | 1.8% by wt. |
| according to Example 3 | — | — | 4.3% by vol. | 1.5% by wt. |
| according to Example 4 | — | — | 4.6% by vol. | 1.4% by wt. |
| according to Example 4 | $CH_2Cl_2$ | 100 | 3.9% by vol. | 2.2% by wt. |

The results according to Table 4 also show that the addition of organic chlorine compounds according to the invention increases the yield of unsaturated carboxylic acid ester and lowers the degree of combustion of the olefin.

What is claimed is:

1. In a process for the manufacture of an unsaturated carboxylic acid ester by the reaction of a member selected from the group consisting of an olefin and a cyclo-olefin, with oxygen and a carboxylic acid in the gaseous phase, in the presence of a catalyst selected from the group consisting of a catalyst which contains elements of subsidiary group VIII of the periodic system, a compound which contains elements of subsidiary group VIII of the periodic system and a combination of said catalyst and said compound, and an alkali metal acetate, at temperatures of from 100° to 250° C. and pressures of from 0.5 to 21 bar absolute, the improvement comprising: said reaction being carried out in the presence of from 1 to 8000 parts per million by weight, calculated on the carboxylic acid used, of an organic chlorine compound selected from the group consisting of:

(a) α-chlorocarboxylic acids having from 1 to 4 carbon atoms and esters thereof with alcohols having from 1 to 4 carbons atoms;

(b) α-chloroaldehydes having from 1 to 4 carbon atoms;

(c) chlorine derivatives of methane having from 1 to 4 chlorine atoms;

(d) chlorine derivatives of methane having from 1 to 3 chlorine atoms and at least one fluorine atom;

(e) chlorine derivatives of ethane and of propane each having at least 2 chlorine atoms; and (f) an admixture thereof.

2. The process according to claim 1, wherein said organic chlorine compound is used in quantities of from 10 to 100 parts per million by weight, calculated on the quantity of carboxylic acid.

3. The process according to claim 1 or 2, wherein said addition of the organic chlorine compound is carried out continuously.

4. The process according to claim 1 or 2, wherein vinyl acetate is manufactured as the unsaturated carboxylic acid ester.

5. The process according to claim 3, wherein vinyl acetate is manufactured as the unsaturated carboxylic acid ester.

* * * * *